United States Patent
Berglund et al.

(10) Patent No.: US 11,007,128 B2
(45) Date of Patent: May 18, 2021

(54) COMPOSITION FOR PREVENTING OR TREATING DENTAL EROSION

(71) Applicant: MEDA OTC AB, Solna (SE)

(72) Inventors: Thomas Berglund, Jar (NO); Gunilla Johansson-Rudén, Askim (SE)

(73) Assignee: MEDA OTC AB

( * ) Notice: Subject to any disclaimer, the term of this patent is extended or adjusted under 35 U.S.C. 154(b) by 0 days.

(21) Appl. No.: 15/315,982

(22) PCT Filed: Jun. 18, 2015

(86) PCT No.: PCT/EP2015/063693
§ 371 (c)(1),
(2) Date: Dec. 2, 2016

(87) PCT Pub. No.: WO2015/193424
PCT Pub. Date: Dec. 23, 2015

(65) Prior Publication Data
US 2017/0087065 A1    Mar. 30, 2017

(30) Foreign Application Priority Data
Jun. 18, 2014    (NO) .................................. 20140766

(51) Int. Cl.
| | | |
|---|---|---|
| *A61K 45/06* | (2006.01) | |
| *A61K 8/21* | (2006.01) | |
| *A61K 51/00* | (2006.01) | |
| *A61Q 11/00* | (2006.01) | |
| *A61K 8/36* | (2006.01) | |
| *A61K 33/16* | (2006.01) | |
| *A61K 9/14* | (2006.01) | |
| *A61K 8/362* | (2006.01) | |
| *A61K 8/365* | (2006.01) | |
| *A61K 8/37* | (2006.01) | |
| *A61K 8/44* | (2006.01) | |
| *A61K 8/368* | (2006.01) | |

(52) U.S. Cl.
CPC .................. *A61K 8/21* (2013.01); *A61K 8/36* (2013.01); *A61K 8/362* (2013.01); *A61K 8/365* (2013.01); *A61K 8/368* (2013.01); *A61K 8/37* (2013.01); *A61K 8/44* (2013.01); *A61Q 11/00* (2013.01)

(58) Field of Classification Search
CPC .......... A61K 8/21; A61K 8/36; A61K 9/4858; A61K 9/0063; A61K 8/368; A61K 47/54; A61K 45/06; A61K 31/215; A61Q 11/00
See application file for complete search history.

(56) References Cited

U.S. PATENT DOCUMENTS

| | | | | |
|---|---|---|---|---|
| 3,337,412 A | * | 8/1967 | Elbreder | A61K 8/21 424/601 |
| 3,413,326 A | | 11/1968 | Schmid | |
| 4,335,102 A | * | 6/1982 | Nakashima | A61K 8/19 424/48 |
| 4,902,497 A | | 2/1990 | Crisanti et al. | |
| 4,902,498 A | * | 2/1990 | Agricola | A61K 8/19 424/52 |
| 5,004,597 A | * | 4/1991 | Majeti | A61K 8/21 424/464 |
| 5,707,610 A | * | 1/1998 | Ibsen | A61K 8/365 424/49 |
| 6,251,369 B1 | | 6/2001 | Stoltz | |
| 2002/0064506 A1 | | 5/2002 | Pellicano et al. | |
| 2003/0157145 A1 | * | 8/2003 | Kalili | A23L 2/52 424/439 |
| 2009/0010856 A1 | | 1/2009 | Rolla et al. | |
| 2009/0087391 A1 | | 4/2009 | Joziak et al. | |
| 2010/0055053 A1 | * | 3/2010 | Ripley | A61K 8/365 424/49 |
| 2010/0260692 A1 | | 10/2010 | Lippert | |
| 2011/0059188 A1 | | 3/2011 | Barbour et al. | |
| 2013/0209375 A1 | | 8/2013 | Moya Argilagos et al. | |
| 2013/0230609 A1 | * | 9/2013 | Modak | A01N 65/44 424/739 |
| 2014/0242000 A1 | | 8/2014 | Rolla et al. | |

FOREIGN PATENT DOCUMENTS

EP    0311260 A2 *   4/1989   ............... A61K 8/21

OTHER PUBLICATIONS

Muhlemann et al "Enamel Solubility Reduction Studies with Inorganic and Organic Fluorides." Helvetica Odontologica Acta, 1957, 1(2), 23-33.
Tyler et al. "Uptake of fluoride by human surface enamel from ammonium bifluoride and consequent reduction in the penetration in vitro by caries-like lesions." Archives Oral Biol. 1984, 29(12), 971-4.
International Search Report for PCT/EP2015/063693, dated Dec. 23, 2015, 4 pages.
Written Opinion of the International Searching Authority for PCT/EP2015/063693, dated Dec. 23, 2015, 6 pages.

* cited by examiner

*Primary Examiner* — Tracy Liu

(57) ABSTRACT

The present invention relates to a composition of pH in the range 2.0 to 4.5 comprising at least one fluoride source and at least one other agent for use in prevention and/or treatment of dental erosion.

14 Claims, 7 Drawing Sheets

15 minutes – after etching

Reference – before etching

HF treatment for 5 minutes and etching for 15 minutes

COMPOSITION FOR PREVENTING OR TREATING DENTAL EROSION

FIELD OF THE INVENTION

The present invention relates to a composition of pH in the range 2.0 to 4.5 comprising at least one fluoride source and at least one organic acid or salt thereof for use in prevention and/or treatment of dental erosion, prevention of demineralisation of the dental enamel and/or enhancement of remineralisation of the dental enamel, prevention of subsurface demineralisation of the dental enamel and/or enhancement of remineralisation of the subsurface dental enamel.

BACKGROUND OF THE INVENTION

Tooth enamel mainly consists of minerals and the primary mineral is hydroxyl apatite (HA), which is a crystalline calcium phosphate with the formula $Ca_5(PO_4)_3(OH)$. Demineralisation of HA starts when the local pH goes below 5.5. The saliva is supersaturated with various ions (see M. J. Larsen et al., "Saturation of human saliva with respect to calcium salts", Archives of Oral Biology (2003) 48, 317-322). These ions act as a buffer, keeping the acidity of the mouth within a certain range, typically pH 6.2 to 7.4. This normally prevents the minerals from dissolving. Some of the mineral loss can be recovered/remineralised from the ions in the saliva if the pH is buffered and stay above 5.5.

Dental/acidic erosion is defined as the irreversible loss of tooth structure (enamel, dentine and cementum) due to chemical dissolution by acids not of bacterial origin. Dental erosion is thus different in both ethology and pathogenesis from dental caries that is an infectious disease caused by certain bacteria in the dental plaque (biofilm). The most common cause of dental erosion is by acidic foods and drinks but can sometimes be caused by gastro-oesophageal reflux. It is the most common chronic disease of children aged 5-17 years according to the U.S. Department of health and Human services (8. Aug 2007).

Dentists have no established good ways to mend already eroded enamel. The best way is to prevent erosion but there are no effective products on the market today.

The use of topical products containing fluoride will result in formation of calcium fluoride ($CaF_2$) precipitate in contact with the enamel. The calcium (Ca) originates from salvia and teeth. $CaF_2$ formation on dental hard tissues during topical fluoride treatment depends on many factors such as the solubility of the tooth, sound or demineralised surface, length of fluoride exposure time, the fluoride concentration and the pH of the topical agent (see Bjørn Øgaard, <<$CaF_2$ Formation: Cariostatic Properties and Factors of Enhancing the Effect>>, Caries Research 2001; 35(suppl 1):40-44.).

Fluorapatite formation following the $CaF_2$ material has been suggested. Fluorapatite $Ca_5(PO_4)_3F$ can be formed in neutral or acidic conditions above pH 4.5 and will dissolve and thus not protect from acidic situations below pH 4.5 such as fruit juices, energy drinks and sodas etc. resulting in erosion of enamel.

An acidic topical product (i.e. below pH of 4.5) containing a small amount of fluoride will after a minor etch release Ca from HA and then instantly be followed by deposition of a thin protective layer of $CaF_2$ on the teeth. The formed low phosphate contaminated $CaF_2$ is only slightly soluble in water and in acidic solutions and much less in saliva (as saliva normally already contains at least 100 mg Calcium/L). $CaF_2$ is much less soluble in acids such as citric acid than the normal enamel hydroxyapatite or fluorapatite. Thus, said low phosphate contaminated $CaF_2$ forms a mechanical barrier that protects dental enamel from acidic erosion.

International patent application with publication no. WO 2005/110347 relates to a composition for inhibiting dental erosion comprising an aqueous solution of hydrofluoric acid (HF) in a concentration of 0.05 to 2.00% in which the pH of the aqueous solution is between 2.5 and 4.5.

C. Hjortsjö et al., "Effect of Stannous Fluoride and Dilute Hydrofluoric Acid on Early Enamel Erosion over Time in vivo", Caries Research 2009; 43:449-454, reports a study made in order to evaluate the longer-term protective effect of aqueous solutions of HF (0.2%, pH 2.0) and stannous fluoride ($SnF_2$) (0.78%, pH 2.9) (both~0.1 mol/l F) on enamel solubility. It was concluded from this study that treatment of sound enamel with a 0.2% HF solution had a protective effect against citric acid attack that lasted for at least 1 week. In contrast, the $SnF_2$ solution containing the same low fluoride concentration had no effect after only 1 day.

SUMMARY OF THE INVENTION

The present invention has surprisingly shown improved results against dental erosion by adding at least one organic acid or salt thereof to a composition of at least one fluoride source.

A main object of the present invention is to provide compositions useful in inhibition of dental erosion which is more effective than those known in the art.

This and other objects are achieved by a composition comprising at least one fluoride source selected from HF, one or more bifluoride(s) or a mixture thereof; and at least one organic acid or salt thereof, wherein at least one pKa of the organic acid is in the range from 2 to 6; wherein the pH of the composition is in the range from 2.0 to 4.5.

According to a preferred embodiment of the present invention, the pH of the composition is in the range from 2.5 to 4.0, more preferable in the range from 3.0 to 3.5, and most preferable about 3.5.

The amount of fluoride in the composition of the present invention is selected from the group consisting of from about 0.01% to about 4.0% by weight, from about 0.01% to about 2.0% by weight, from about 0.01% to about 1.0% by weight, from about 0.01% to about 0.5% by weight, from about 0.01% to about 0.05% by weight and less than 0.05% by weight.

According to a preferred embodiment of the present invention, the amount of fluoride in the composition is from about 0.01% to about 1.0% by weight, more preferable from about 0.01% to about 0.5% by weight, most preferable about 0.15% by weight.

According to one aspect of the present invention, the at least one fluoride source is selected from the group consisting of HF, $NaHF_2$, $KHF_2$, $NH_4HF_2$ and any mixtures thereof.

According to a preferred embodiment of the present invention, the at least one fluoride source is HF.

According to another preferred embodiment of the present invention, the at least one fluoride source is a bifluoride. The bifluoride is preferably selected from the group consisting of $NaHF_2$, $KHF_2$, $NH_4HF_2$ and any mixtures thereof.

In addition to the at least one fluoride source defined above, the composition of the invention may include a further fluoride source, for example selected from the group consisting of NaF, KF, $NH_4F$ and mixtures thereof.

According to one embodiment of the invention, the fluoride source is a mixture of HF and one or more bifuoride(s).

According to another embodiment of the invention, the fluoride source is a mixture of HF and another fluoride, for example selected from the group consisting of NaF, KF, $NH_4F$ and mixtures thereof.

According to further embodiment of the invention, the fluoride source is a mixture of one or more bifluoride(s) and a further fluoride, for example selected from the group consisting of NaF, KF, $NH_4F$ and mixtures thereof.

According to yet another embodiment of the invention, the fluoride source is a mixture of HF, one or more bifluoride(s), and a further fluoride, for example selected from the group consisting of NaF, KF, $NH_4F$ and mixtures thereof.

According to another aspect of the present invention it is a proviso that the composition does not comprise acidulated phosphate fluorides.

According to a preferred embodiment of the present invention, the at least one organic acid or salt thereof is physiologically acceptable.

In another preferred embodiment of the invention, the at least one organic acid or salt thereof of the composition is selected from the group consisting of benzoic acid, sodium benzoate, glycine, glycolic acid, glutamic acid, lactic acid and any mixtures thereof.

The amount of organic acid(s) or salts thereof in the composition of the present invention is selected from the group consisting of from about 0.01% to about 10.0% by weight, from about 0.01% to about 7.0% by weight, from about 0.01% to about 3.0% by weight, from about 0.01% to about 2.0% by weight, from about 0.10% to about 2.0% by weight, from about 0.01% to about 1.0% by weight, from about 0.10% to about 1.0% by weight, and from about 0.10% to about 0.5% by weight.

In a preferred embodiment of the present invention, each of the organic acids or salts thereof present in the composition is in an amount of from about 0.10% to about 2.0% by weight, more preferably from about 0.10% to about 1.0% by weight, and most preferably from about 0.10% to about 0.5% by weight.

In a preferred embodiment of the present invention, glycine is present in the composition in an amount of from about 0.10% to about 10.0% by weight, from about 0.10% to about 7.0% by weight, from about 0.10% to about 5.0% by weight, from about 0.10% to about 3.0% by weight, from about 0.10% to about 2.0% by weight, from about 0.10% to about 1.0% by weight, from about 0.10% to about 0.5% by weight or from about 0.10% to about 0.3% by weight. One or more other organic acid(s) or salt thereof may be present in the composition in addition to the glycine.

In another preferred embodiment of the present invention, benzoic acid is present in the composition in an amount of from about 0.05% to about 2.0% by weight, from about 0.10% to about 1.0% by weight, or from about 0.10% to about 0.5% by weight. One or more other organic acid(s) or salt thereof may be present in the composition in addition to the benzoic acid.

In a further preferred embodiment of the present invention, sodium benzoate is present in the composition in an amount of from about 0.05% to about 2.0% by weight, from about 0.10% to about 1.0% by weight, or from about 0.10% to about 0.5% by weight. One or more other organic acid(s) or salt thereof may be present in the composition in addition to the sodium benzoate.

In yet another preferred embodiment of the present invention, glycine and benzoic acid, or glycine and sodium benzoate are present in the composition. The amount of each of organic acid or salt is in the amount from about 0.05% to about 2.0% by weight, from about 0.10% to about 1.0% by weight, or from about 0.10% to about 0.5% by weight of the composition.

According to still another embodiment of the invention, glycine and glycolic acid, glycine and glutamic acid, or glycine and lactic acid are present in the composition. The amount of each of organic acid or salt is in the amount from about 0.05% to about 2.0% by weight, from about 0.10% to about 1.0% by weight, or from about 0.10% to about 0.5% by weight of the composition.

According to one aspect of the present invention, at least part of the fluoride source is in particulate form.

According to another aspect of the present invention, the composition is in the form of an aqueous solution, a gel, a foam, a dentifrice, a dental varnish or a toothpaste.

According to another aspect of the present invention, the composition is in form of a fluid on application and sets as a varnish on the teeth in temperatures above 30° C.

According to a preferred embodiment of the present invention, the composition is in the form of a toothpaste comprising a bifluoride in particulate form.

According to another preferred embodiment, the composition is in a form of an aqueous solution that is used in the same way as a mouth rinse.

In one embodiment of the present invention, the composition may comprise a further agent being a water soluble polymer. The polymer may be selected from the group consisting of a polysaccharide, a polysaccharide derivative, a poloxamer and a polyethylene glycol (PEG). The polymer may be present in the composition in an amount of 0.1% to 10% by weight.

According to one embodiment of the present invention, polymer is a chitosan and a chitosan derivative.

In one embodiment of the present invention, the composition may further comprise a divalent metal ion. The divalent metal ion may be present in the composition in an amount of 0.01% to 0.5% by weight. The divalent metal ion is selected from the group consisting of Ca, Zn, Cu and Sn.

In one embodiment of the present invention, the composition may further comprise an antibacterial agent. The antibacterial agent may be selected from bis-biguanide and quaternary ammonium compounds or any combination thereof. Zn and Cu as mentioned above are antibacterial agents as well. According to one embodiment, the antibacterial agent is chlorhexidine and the chlorhexidine is present in the composition in an amount of 0.001% to 1% by weight.

The present composition according to the invention is for use in prevention and/or treatment of dental erosion.

In another aspect the present invention the composition as defined above is for use in preventing demineralisation of the dental enamel and/or enhancing remineralisation of the dental enamel.

In yet another aspect the present invention the composition as defined above is for use in preventing subsurface demineralisation of the dental enamel and/or enhancing remineralisation of the subsurface dental enamel.

DESCRIPTION OF THE FIGURES

Preferred embodiments of the present invention will now be illustrated in more detail with reference to the accompanying figures.

DETAILED DESCRIPTION OF THE INVENTION

Experiments were performed to study the compositions' effect on dental erosion.

A Comparison Example was performed to show that polished HA discs are an appropriate in vitro model for studying effects of fluoride solutions and etching on enamel.

Figure 1:
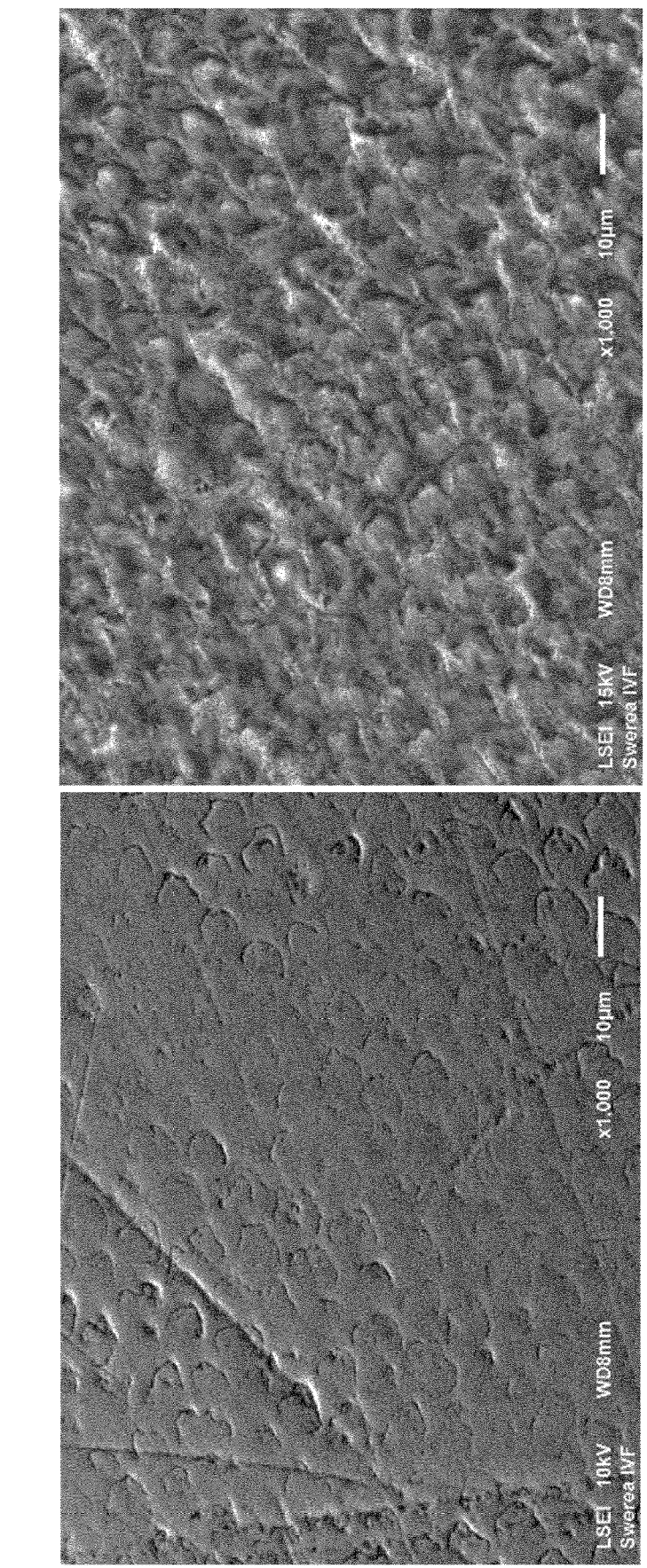
FIG. 1 illustrates SEM pictures of an untreated HA disc before and after etching.
Figure 2:
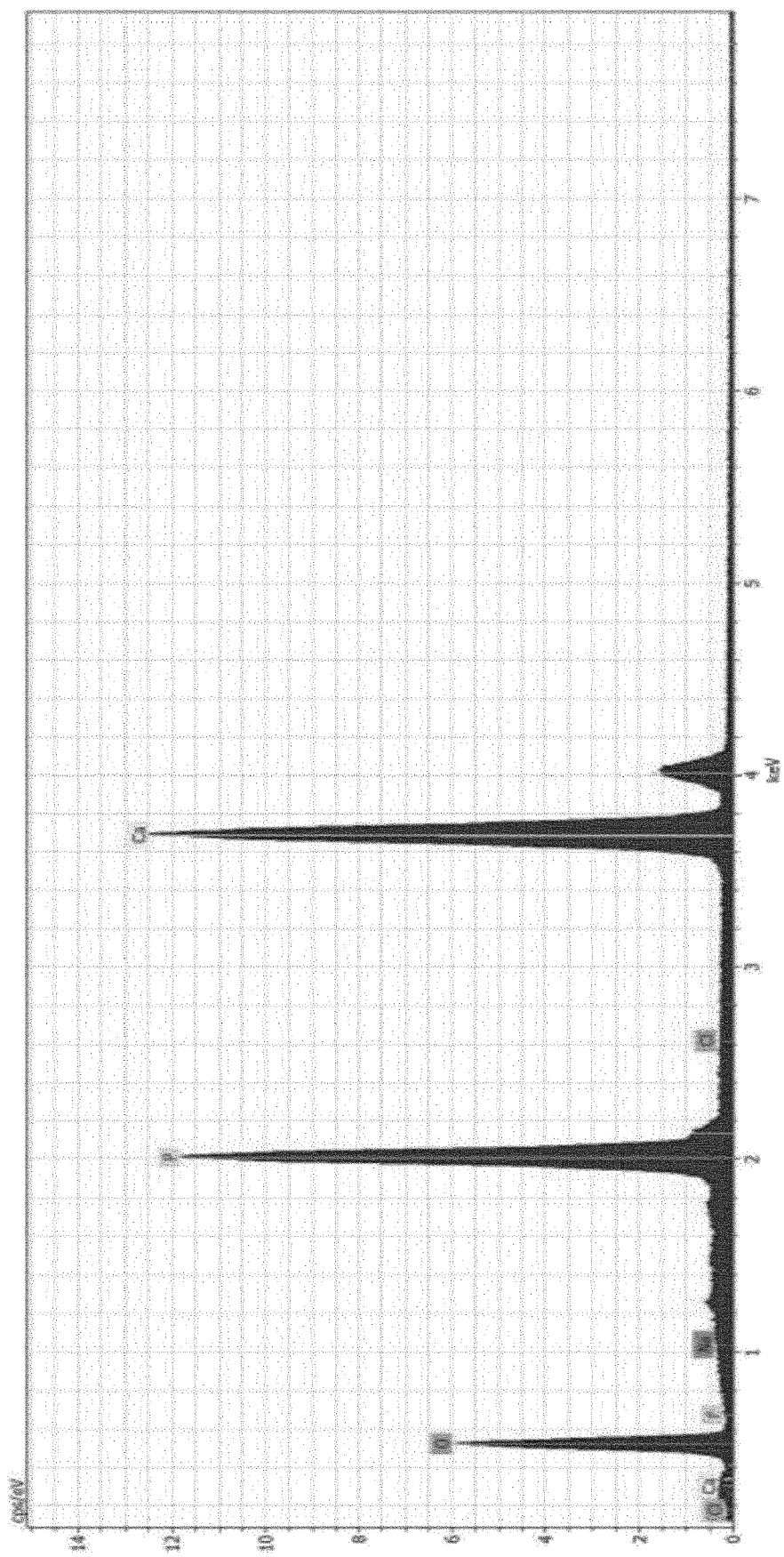
FIG. 2 shows an EDS spectra of an untreated HA disc.

Reference Example 1 shows SEM pictures of an untreated HA disc before and after etching (see FIG. 1), and EDS spectrum of the presence of oxygen (O), phosphor (P) and calcium (Ca) proving that hydroxyl apatite $Ca_5(PO_4)_3(OH)$ is formed on the surface of the untreated HA disc (see FIG. 2).

Figure 3:
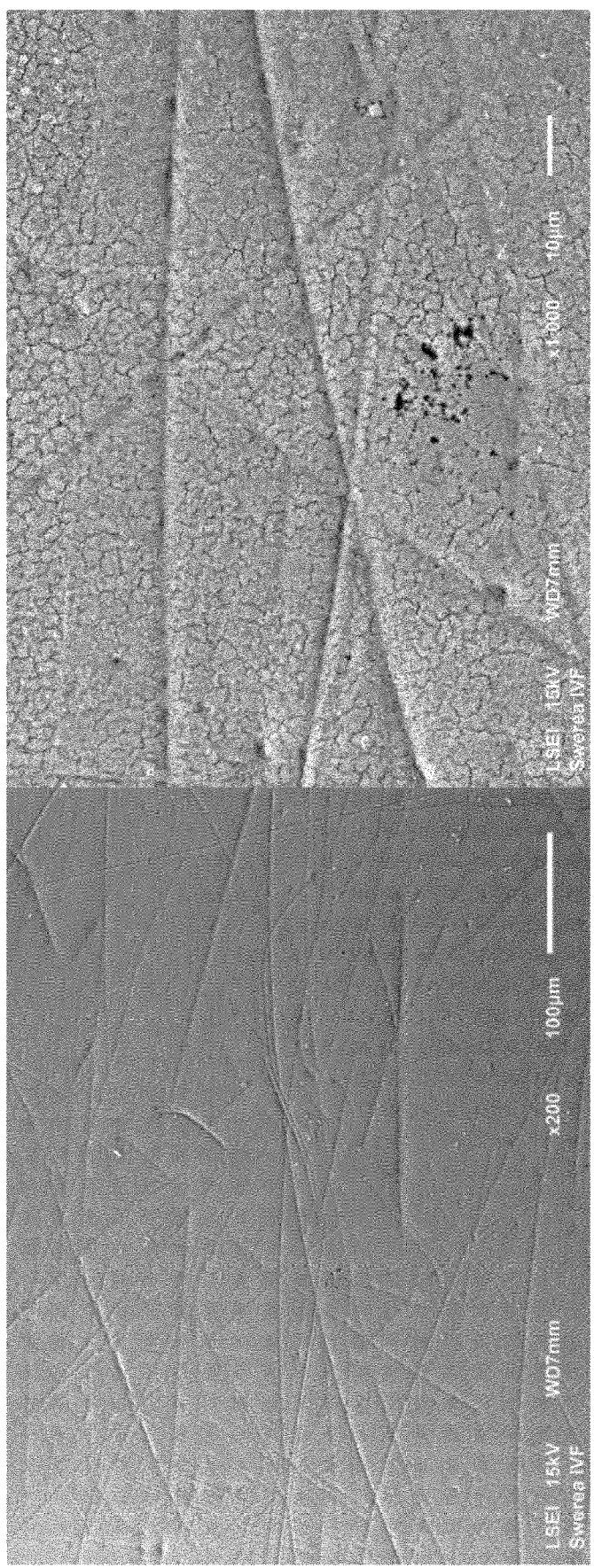
FIG. 3 illustrates SEM pictures of a HA disc treated with a solution of Table 1 before and after etching, and compared to FIG. 1 this HA disc is protected from the etching.
Figure 4:
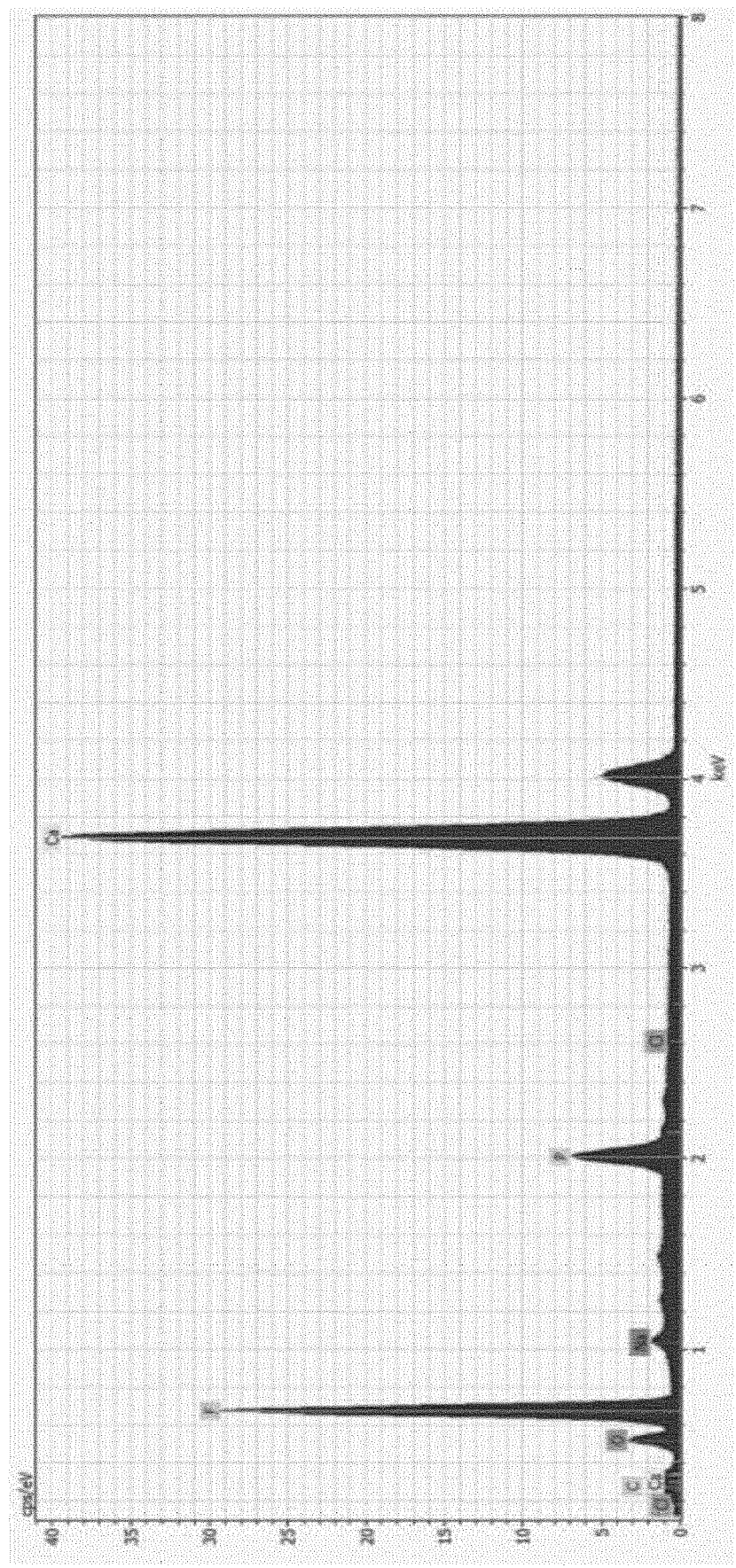
FIG. 4 shows an EDS spectra of the HA disc after treatment with the solution of Table 1.

Example 1 shows corresponding date as presented in Reference Example 1 for a HA disc treated with a composition of the invention (see FIGS. 3 and 4).

Reference Example 2 shows an experiment with a composition according to the prior art (WO 2005/110347) wherein the fluoride source is hydrogen fluoride (HF). No organic acids or salts thereof are added.

Examples 1 to 10 show experiments with compositions of the invention wherein the fluoride source is HF. Different organic acids or salts thereof are present in the various compositions. The amounts of HF and organic acid(s)/salt(s) are varied, as well as the pH value.

As can be seen from Examples 1 to 10, as shown by ICP-AES analysis, all compositions according to the invention are more effective in inhibiting dental erosion than the composition of Reference Example 2.

Reference Example 3 shows an experiment with a composition wherein the fluoride source is a bifluoride (i.e. $NaHF_2$). No organic acids or salts thereof are added.

Examples 11 to 12 show experiments with compositions of the invention wherein the fluoride source is a bifluoride (i.e. $NaHF_2$). Different organic acids are present in the various compositions.

As can be seen from Examples 11 and 12, as shown by ICP-AES analysis, the compositions according to the invention are more effective in inhibition of dental erosion than the composition of Reference Example 2 not comprising an organic acid or salt thereof.

Experimental Model

The method used is an in vitro model consisting of hydroxyl apatite (HA) discs which serve as a model for tooth enamel. The model enables testing the effect on preventing enamel erosion after acid etching by using different solutions containing fluoride (F). As shown by the Comparison Example below, this is a good in vitro model for studying effects of aqueous fluoride solutions and etching on enamel.

Analytical Methods

Analyses were carried out by using low vacuum scanning electron microscopy (SEM) equipped with energy-dispersive X-ray spectroscopy (EDS) detectors for elemental analysis of disc surfaces and inductively coupled plasma atomic emission spectroscopy (ICP-AES) analysis of the etching solution.

SEM

In general, SEM produces images of a sample by scanning it with a focused beam of electrons. The electrons interact with atoms in the sample, producing various signals that can be detected and that contain information about the sample's surface topography and composition. Specimens can be observed in high vacuum, in low vacuum, in wet conditions. In the present analyses, low vacuum conditions have been used.

EDS detectors as used in the present SEM, have analytical capabilities, and can provide several items of data at each pixel.

In the examples below, SEM analysis enables a visual comparison of the surface layers, i.e. $CaF_2$ layer formed upon fluoride treatment of the HA discs, as well as elemental analysis and comparison of the layer thickness. EDS is preferably run to compare the amount of fluoride (F), phosphor (P) and calcium (Ca) on the disc surface. An increase in Ca and F in combination with a decrease in P after fluoride treatment means that a $CaF_2$ layer has been formed on the surface. After etching, peaks of Ca and F usually decrease and P increases.

ICP-AES

In general, ICP-AES is an analytical technique used for the detection of trace metals. It is a type of emission spectroscopy that uses the inductively coupled plasma to produce excited atoms and ions that emit electromagnetic radiation at wavelengths characteristic of a particular element. The intensity of this emission is indicative of the concentration of the element within the sample.

In the examples below, erosion corresponds to surface dissolution and when HA is dissolved there are ions released into the acid. Difference in amount dissolved HA as Ca and P (mg/L) are found. The interpretation of the data is; when there is less Ca and P found in the citric acid after fluoride treatment compared to a citric acid etched control HA-disc, then the fluoride treatment has proven to protect the disc. That is, ICP-AES analysis measures the amount of Ca and P ions in the etching solutions. Ca and P concentration in mg/l or μg/l of etching solutions are compared to results of etching solution of an untreated reference HA disc and the percentage reduction of Ca and P is calculated. This percentages indicate how well the HA discs are protected from etching. The lower concentrations of Ca and P ions, the higher resistance against etching/erosion.

COMPARISON EXAMPLE

Equipment

A low vacuum scanning electron microscope, JEOL JSM 6610 LV, was used for studying surfaces.

SEM pictures were taken with 5000 times magnification (SEM×5000).

Hydroxyl Apatite (HA) Discs

HA discs were prepared. The discs had one polished side and one unpolished. The discs were stored at room temperature and kept dry.

Figure 5:
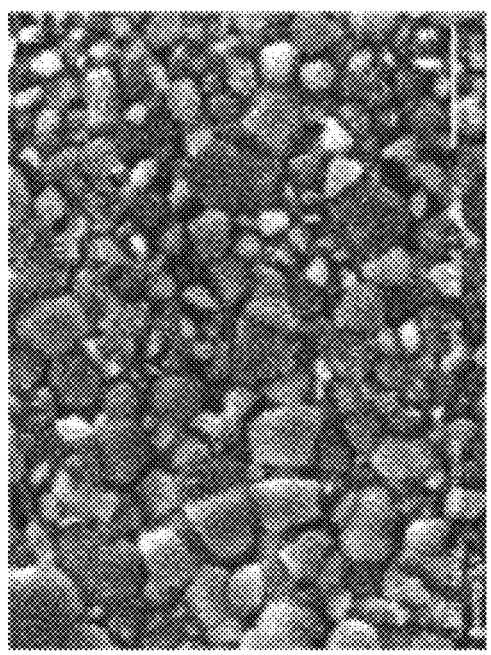
FIG. 5 depicts SEM pictures (×5000) taken to analyse the HA surface before and after etching with citric acid.
Figure 5:
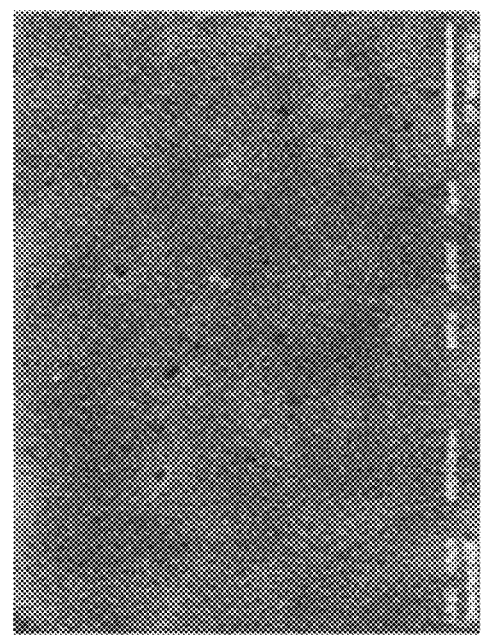

3 drops of 2% citric acid were placed on a HA disc using a pipette. The 3 drops were allowed to etch the HA disc for 15 minutes at room temperature. The contours of the drops were clearly defined and there was obviously a surface tension. The HA disc was then rinsed in distilled water and then left to dry on tissue paper. FIG. 5 depicts SEM pictures (×5000) taken to analyse the HA surface before and after etching with citric acid.

Figure 6:
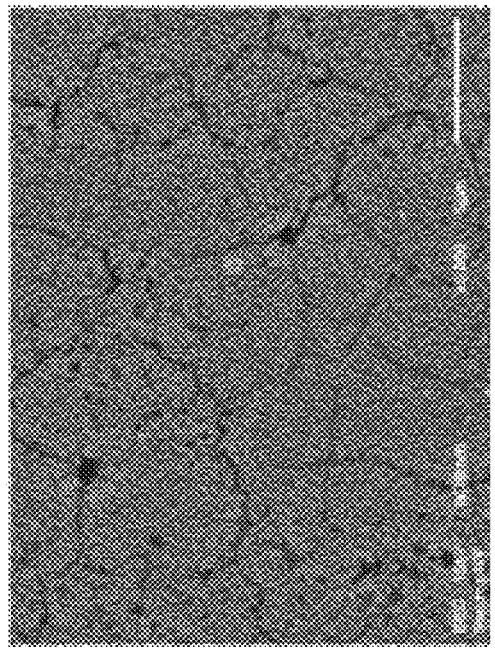
FIG. 6 depicts a SEM picture (×5000) taken to analyse the HA surface after HF treatment.

A HA disc were immersed in a solution comprising 0.15% hydrogen fluoride (HF) at pH 2.58 for 5 minutes in 37° C. during gentle agitation (50 ml plastic bottle was used). The disc was rinsed in distilled water and left to dry on tissue paper for a few minutes. 3 droplets of 2% citric acid were placed on the surface by using a syringe, and the etching was allowed for 15 minutes. Visual inspection of the disc surface showed that after treatment with HF solution, the surface tension had decreased and the droplets of acid floated out compared to the disc that was not HF treated. The disc was then rinsed in distilled water. FIG. 6 depicts a SEM picture (×5000) taken to analyse the HA surface after HF treatment.

Ex vivo Human Tooth

A human ex vivo tooth (premolar) was received from a dentist practice. The tooth was stored in Ringer solution and kept in refrigerator.

The effect of the HF treatment on HA surfaces was verified using an ex vivo human premolar tooth. The tooth had been split into two halves before the experiment (tooth 1:1 and tooth 1:2). The two tooth halves were rinsed with distilled water. One tooth half was placed in a 50 ml plastic bottle containing 2% citric acid and then allowed to incubate at 37° C. for 15 minutes under gentle agitation. The tooth was then rinsed with distilled water for a few minutes and then put on tissue paper to dry. The other tooth half was immersed in a solution comprising 0.15% hydrogen fluoride (HF) at pH 2.58 for 5 minutes at 37° C. under gentle agitation (50 ml plastic bottle). The tooth half was rinsed with distilled water and then immersed in 2% citric acid and then allowed to incubate at 37° C. for 15 minutes under gentle agitation. The tooth was then rinsed with distilled water and left to dry on tissue paper for a few minutes.

Figure 7:
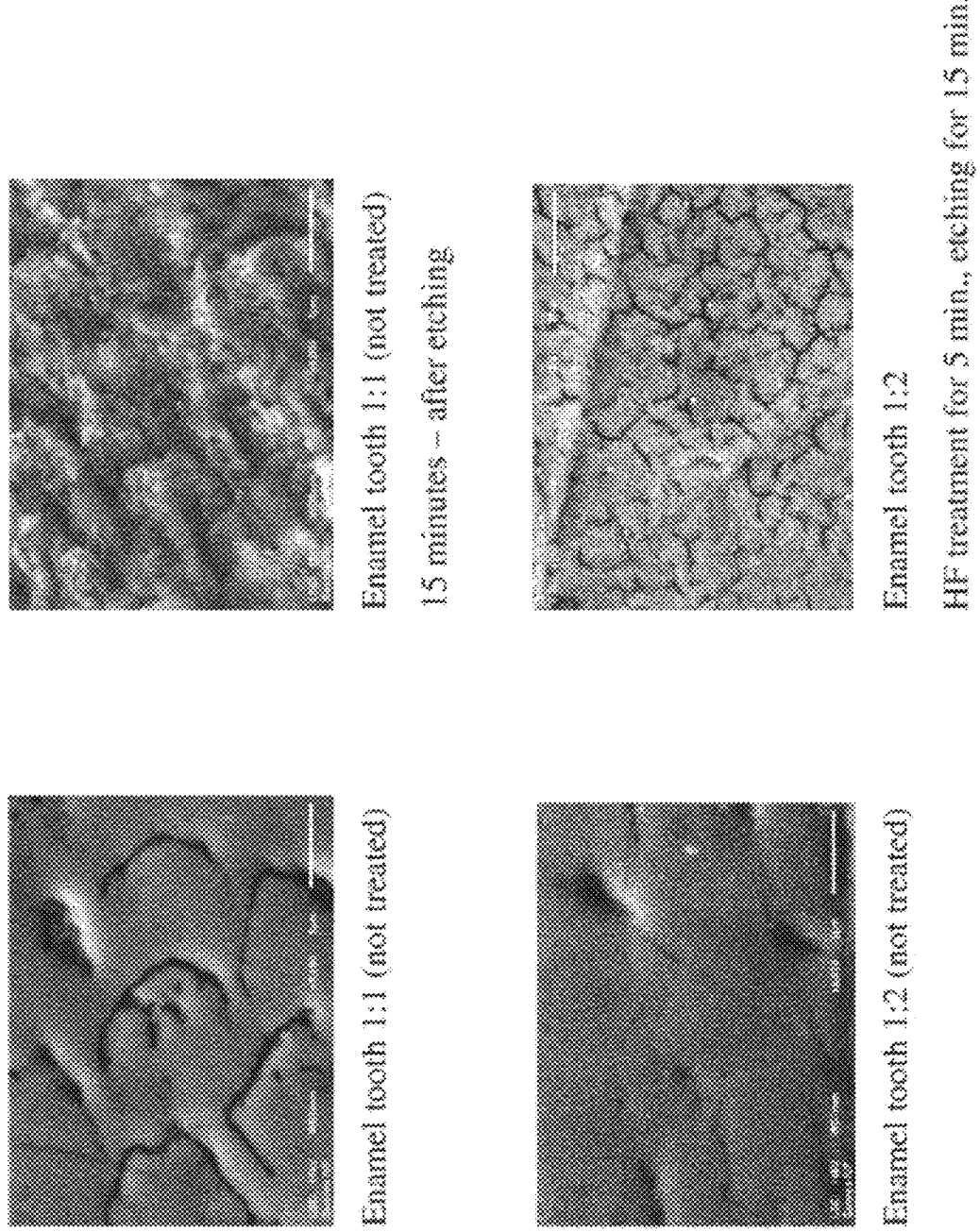
FIG. 7 depicts SEM pictures (×5000) taken to study the effect of HF treatment and subsequent citric acid etching on the enamel surface.

FIG. 7 depicts SEM pictures (×5000) taken to study the effect of HF treatment and subsequent citric acid etching on the enamel surface.

The SEM pictures depicted in FIG. 7 show that the enamel is clearly protected from etching by the $CaF_2$ layer formed during HF treatment.

Conclusion of Comparison Example

Polished HA discs appear to be a good in vitro model for studying effects of fluoride solutions and etching on enamel.

Materials, Conditions and Routines used in the following Reference Examples and Examples 2% citric acid (pH 2.2) was used as etching solution.
Distilled water or tap water was used for rinsing.
All steps of the experiments were performed at 20 to 25° C.

Fluoride solutions were weighed into plastic beakers and one or more HA discs were placed into each beaker for 5 minutes. Then the discs were moved to a container with water to be rinsed for at least 5-10 seconds.

Etching solution was weighed into plastic bottles and one fluoride treated HA discs were placed in each bottle for 15 minutes. Then the discs were moved to a container with water to be rinsed for at least 5-10 seconds.

The disc surface after etching were analysed with SEM.
The citric acid solution used in the studies was subjected to ICP-AES analysis.

REFERENCE EXAMPLE 1

A low vacuum scanning electron microscope, JEOL JSM 6610 LV, was used for studying surfaces and equipped with EDS for elemental analysis.

SEM pictures (SEM×1000) of an untreated HA disc before (on the left) and after etching (on the right) are shown in FIG. 1.

In FIG. 2 an EDS spectrum of an untreated HA disc showing the presence of oxygen (O), phosphor (P) and calcium (Ca) in proportions telling that it is hydroxyl apatite $Ca_5(PO_4)_3(OH)$ on the surface.

REFERENCE EXAMPLE 2

A solution consisting of the ingredients shown in the table below was prepared:

TABLE

| (Reference solution 2) | |
|---|---|
| Ingredient | Amount in % (w/w) |
| Hydrogen fluoride | 0.15 |
| Purified water | up to 100 |
| NaOH | Adjustment of pH to 3.5 |

The following results were obtained.

| | ICP Citric acid etch | |
|---|---|---|
| | 15 min 2% citric acid etch (room temp) | |
| Product | Reduction Ca % | Reduction P % |
| Reference solution 2 | 60 | 66 |

EXAMPLE 1

A solution consisting of the ingredients shown in table 1 was prepared:

TABLE 1

| Ingredient | Amount in % (w/w) |
|---|---|
| Hydrogen fluoride | 0.15 |
| Glycine | 0.20 |
| Sodium benzoate | 0.15 |
| Sweetener, viscosity improver, taste etc. | 36 |
| Purified water | 63 |
| HCl or NaOH | Adjustment of pH to 3.5 |

The total amount of fluoride in the composition was 0.14%.

A low vacuum scanning electron microscope, JEOL JSM 6610 LV, was used for studying surfaces and equipped with EDS for elemental analysis.

SEM pictures of a HA disc treated with the solution of Table 1 before (on the left, SEM×200) and after etching (on the right, SEM×1000)) are shown in FIG. 3. The protective layer is somewhat affected after 15 min etching but mainly intact and the tooth beneath is protected.

EDS spectrum of the HA disc after treatment with the solution of Table 1 showing the presence of F and Ca in proportions telling that it is $CaF_2$ is shown in FIG. 4 The amounts of O and P are suppressed due to the covering layer of is $CaF_2$ but still visible in the spectra because EDS penetrates deeper into the specimen than the layer. The spectrum also shows that the layer does not consist of fluorapatite $Ca_5(PO_4)_3F$ due to the proportions in the spectrum.

Amount released P and Ca compared to control (untreated) was noted and the treatment with the solution of Table 1 had a major protective impact as showed by the reduction of amount eroded ions:

$$\% \text{ reduction} = \frac{(\text{release from Control (untreated)} - \text{treated})}{\text{release from Control}} \times 100$$

| | ICP Citric acid etch 15 min 2% citric acid etch (room temp) | |
|---|---|---|
| Product | Reduction Ca % | Reduction P % |
| Solution of Table 1 | 73 | 79 |

EXAMPLE 2

A solution consisting of the ingredients shown in table 1 except that the amount of sodium benzoate was increased to 0.30% and the amount of purified water was decreased accordingly, was prepared and tested. The total amount of fluoride in the composition was 0.14%, and the acidity was adjusted to pH 3.5.

The surfaces of the HA discs treated with the present solution before and after etching were significantly improved over that treated by the solution of Table 1.

The following results were obtained.

| | ICP Citric acid etch 15 min 2% citric acid etch (room temp) | |
|---|---|---|
| Product | Reduction Ca % | Reduction P % |
| Solution of Example 2 | 79 | 85 |

EXAMPLE 3

A solution consisting of the ingredients shown in table 3 was prepared:

TABLE 3

| Ingredient | Amount in % (w/w) |
|---|---|
| Hydrogen fluoride | 0.15 |
| Glycine | 0.90 |
| Purified water | up to 100 |
| HCl or NaOH | Adjustment of pH to 3.5 |

The total amount of fluoride in the composition was 0.14%.

The following results were obtained.

| | ICP Citric acid etch 15 min 2% citric acid etch (room temp) | |
|---|---|---|
| Product | Reduction Ca % | Reduction P % |
| Solution of Table 3 | 72 | 61 |

EXAMPLE 4

A solution consisting of the ingredients shown in table 4 was prepared:

TABLE 4

| Ingredient | Amount in % (w/w) |
|---|---|
| Hydrogen fluoride | 0.48 |
| Glycine | 0.56 |
| Purified water | up to 100 |
| HCl or NaOH | Adjustment of pH to 3.51 |

The total amount of fluoride in the composition was 0.5%.

The following results were obtained.

| | ICP Citric acid etch 15 min 2% citric acid etch (room temp) | |
|---|---|---|
| Product | Reduction Ca % | Reduction P % |
| Solution of Example 12 | 89 | 86 |

EXAMPLE 5

A solution consisting of the ingredients shown in table 5 was prepared:

TABLE 5

| Ingredient | Amount in % (w/w) |
|---|---|
| Hydrogen fluoride | 0.15 |
| Glycine | 0.20 |
| Purified water | up to 100 |
| HCl or NaOH | Adjustment of pH to 2.58 |

The total amount of fluoride in the composition was 0.14%.

The following results were obtained.

| | ICP Citric acid etch 15 min 2% citric acid etch (room temp) | |
|---|---|---|
| Product | Reduction Ca % | Reduction P % |
| Solution of Table 5 | 61 | 83 |

EXAMPLE 6

A solution consisting of the ingredients shown in table 6 was prepared:

TABLE 6

| Ingredient | Amount in % (w/w) |
|---|---|
| Hydrogen fluoride | 0.95 |
| Glycine | 1.34 |

TABLE 6-continued

| Ingredient | Amount in % (w/w) |
|---|---|
| Purified water | up to 100 |
| HCl or NaOH | Adjustment of pH to 3.87 |

The total amount of fluoride in the composition was 1%. The following results were obtained.

| | ICP Citric acid etch 15 min 2% citric acid etch (room temp) | |
|---|---|---|
| Product | Reduction Ca % | Reduction P % |
| Solution of Table 6 | 65 | 71 |

EXAMPLE 7

A solution consisting of the ingredients shown in table 7 was prepared:

TABLE 7

| Ingredient | Amount in % (w/w) |
|---|---|
| Hydrogen fluoride | 0.95 |
| Glycine | 1.34 |
| Sodium benzoate | 0.30 |
| Purified water | up to 100 |
| HCl | Adjustment of pH to 3.9 |

The following results were obtained.

| | ICP Citric acid etch 15 min 2% citric acid etch (room temp) | |
|---|---|---|
| Product | Reduction Ca % | Reduction P % |
| Solution of Table 7 | 67 | 81 |

EXAMPLE 8

A solution consisting of the ingredients shown in table 8 was prepared:

TABLE 8

| Ingredient | Amount in % (w/w) |
|---|---|
| Hydrogen fluoride | 0.15 |
| Glycine | 0.20 |
| Glycolic acid | 0.30 |
| Purified water | up to 100 |
| NaOH | Adjustment of pH to 3.5 |

The following results were obtained.

| | ICP Citric acid etch 15 min 2% citric acid etch (room temp) | |
|---|---|---|
| Product | Reduction Ca % | Reduction P % |
| Solution of Table 8 | 76 | 77 |

EXAMPLE 9

A solution consisting of the ingredients shown in table 9 was prepared:

TABLE 9

| Ingredient | Amount in % (w/w) |
|---|---|
| Hydrogen fluoride | 0.15 |
| Glutamic acid | 0.30 |
| Purified water | up to 100 |
| NaOH | Adjustment of pH to 3.5 |

The following results were obtained.

| | ICP Citric acid etch 15 min 2% citric acid etch (room temp) | |
|---|---|---|
| Product | Reduction Ca % | Reduction P % |
| Solution of Table 9 | 69 | 70 |

EXAMPLE 10

A solution consisting of the ingredients shown in table 10 was prepared:

TABLE 10

| Ingredient | Amount in % (w/w) |
|---|---|
| Hydrogen fluoride | 0.15 |
| Glycine | 0.20 |
| Lactic acid | 0.30 |
| Purified water | up to 100 |
| NaOH | Adjustment of pH to 3.5 |

The following results were obtained.

| | ICP Citric acid etch 15 min 2% citric acid etch (room temp) | |
|---|---|---|
| Product | Reduction Ca % | Reduction P % |
| Solution of Table 10 | 66 | 70 |

REFERENCE EXAMPLE 3

A solution consisting of the ingredients shown in the table below was prepared:

TABLE (Reference solution 3)

| Ingredient | Amount in % (w/w) |
|---|---|
| $NaHF_2$ | corr. to 0.14% F |
| Purified water | up to 100 |

TABLE-continued (Reference solution 3)

| Ingredient | Amount in % (w/w) |
|---|---|
| HCl | Adjustment of pH to 3.5 |

The total amount of fluoride in the composition was 0.14%.

The following results were obtained.

| | ICP Citric acid etch 15 min 2% citric acid etch (room temp) | |
|---|---|---|
| Product | Reduction Ca % | Reduction P % |
| Reference solution 3 | 47 | 56 |

EXAMPLE 11

A solution consisting of the ingredients shown in table 11 was prepared:

TABLE 11

| Ingredient | Amount in % (w/w) |
|---|---|
| NaHF$_2$ | corr. to 0.14% F |
| Glycine | 0.20 |
| Purified water | up to 100 |
| HCl or NaOH | Adjustment of pH to 3.5 |

The following results were obtained.

| | ICP Citric acid etch 15 min 2% citric acid etch (room temp) | |
|---|---|---|
| Product | Reduction Ca % | Reduction P % |
| Solution of Table 11 | 55 | 66 |

EXAMPLE 12

A solution consisting of the ingredients shown in table 12 was prepared:

TABLE 12

| Ingredient | Amount in % (w/w) |
|---|---|
| NaHF$_2$ | corr. to 0.14% F |
| Benzoic acid | 0.30 |
| Purified water | up to 100 |
| HCl or NaOH | Adjustment of pH to 3.5 |

The following results were obtained.

| | ICP Citric acid etch 15 min 2% citric acid etch (room temp) | |
|---|---|---|
| Product | Reduction Ca % | Reduction P % |
| Solution of Table 12 | 73 | 81 |

The invention claimed is:

1. A composition comprising,
   at least one bifluoride selected from the group consisting of NaHF$_2$, KHF$_2$, and NH$_4$HF$_2$; and
   benzoic acid;
   wherein the composition is a toothpaste and the at least one bifluoride is provided in the toothpaste in particulate form;
   wherein the pH of the composition is in the range from 2.0 to 4.5, and
   wherein the total amount of benzoic acid present in the composition is between about 0.1% and about 0.5% by weight; and
   the total amount of the at least one bifluoride is between about 0.01% and about 0.5% by weight.

2. The composition according to claim 1, wherein the pH of the composition is in the range from 2.5 to 4.0.

3. The composition according to claim 2, wherein the pH of the composition is in the range from 3.0 to 3.5.

4. The composition according to claim 2, wherein the pH of the composition is about 3.5.

5. The composition according to claim 1, wherein the total amount of benzoic acid present in the composition is between about 0.2% and 0.3% by weight.

6. The composition according to claim 1, wherein the total amount of the at least one bifluoride present in the composition is about 0.15% by weight.

7. The composition according to claim 1, wherein the at least one bifluoride is NaHF$_2$.

8. A method for preventing and/or treating dental erosion, preventing demineralization or subsurface demineralization of the dental enamel, and/or enhancing remineralization of the dental enamel or the subsurface dental enamel, the method comprising
   administering to a subject in need thereof a composition comprising one or more bifluoride(s) selected from the group consisting of NaHF$_2$, KHF$_2$, and NH$_4$HF$_2$; and benzoic acid;
   wherein the composition is a toothpaste and the at least one bifluoride is provided in the toothpaste in particulate form;
   wherein the pH of the composition is in the range from 2.0 to 4.5, and wherein the total amount of benzoic acid present in the composition is between about 0.1% and about 0.5% by weight; and
   wherein the total amount of the at least one bifluoride is between about 0.01% and about 0.5% by weight.

9. The method of claim 8, wherein the pH of the composition is in the range from 2.5 to 4.0.

10. The method of claim 8, wherein the pH of the composition is in the range from 3.0 to 3.5.

11. The method of claim 8, wherein the pH of the composition is about 3.5.

12. The method of claim 8, wherein the total amount benzoic acid present in the composition is about 0.2% and 0.3% by weight.

13. The method of claim 8, wherein the total amount of the at least one bifluoride present in the composition is about 0.15% by weight.

14. The method of claim 8, wherein the at least one bifluoride is $NaHF_2$.

* * * * *